United States Patent [19]

Kamen

[11] 4,137,915

[45] Feb. 6, 1979

[54] FLOW CONTROL FOR AN INTRAVENOUS FEEDING SYSTEM

[76] Inventor: Dean Kamen, 99 Bulson Rd., Rockville Centre, N.Y. 11570

[21] Appl. No.: 803,073

[22] Filed: Jun. 3, 1977

[51] Int. Cl.² .............................................. A61M 5/14
[52] U.S. Cl. ........................ 128/214 E; 128/DIG. 13; 222/58; 340/613
[58] Field of Search ........... 128/214 R, 214 E, 214 F, 128/214.2, DIG. 12, DIG. 13; 340/272; 222/58; 200/85 R

[56] References Cited

U.S. PATENT DOCUMENTS

| | | | |
|---|---|---|---|
| 2,865,371 | 12/1958 | Dorbecker et al. | 128/214 F |
| 3,105,490 | 10/1963 | Schoenfeld | 128/214 E |
| 3,425,415 | 2/1969 | Gordon et al. | 128/214 F |
| 3,749,285 | 7/1973 | Latham | 222/58 |
| 4,038,981 | 8/1977 | LeFevre et al. | 128/214 E |

*Primary Examiner*—Dalton L. Truluck
*Attorney, Agent, or Firm*—Bauer & Amer

[57] ABSTRACT

The flow control hereof is applied to a known system of feeding a patient intravenously and contemplates the use of a clamp applied externally to the delivery tube extending from the intravenous bag, bottle or other appropriate container to the patient, said clamp being selectively successively opened and then closed to correspondingly meter the feeding flow of the intravenous fluid on a selected volume per time basis, e.g. 1 cc/minute, so that intravenous feeding of the patient is achieved according to a desired time schedule. The external application of the clamp does not detract from conventional sterile conditions of the system. Also, and most important, the operation of the clamp is related to the weight of the intravenous fluid, which weight, if the feeding is proceeding as it should, should progressively diminish in a predictable way. The flow control hereof thus allows uninterrupted flow if the weight is not diminishing at the rate that it should; or it terminates flow, if the rate is too rapid. In this effective way, the flow control hereof thus correspondingly effectively supervises the intravenous feeding so that it is achieved according to a desired time schedule.

2 Claims, 3 Drawing Figures

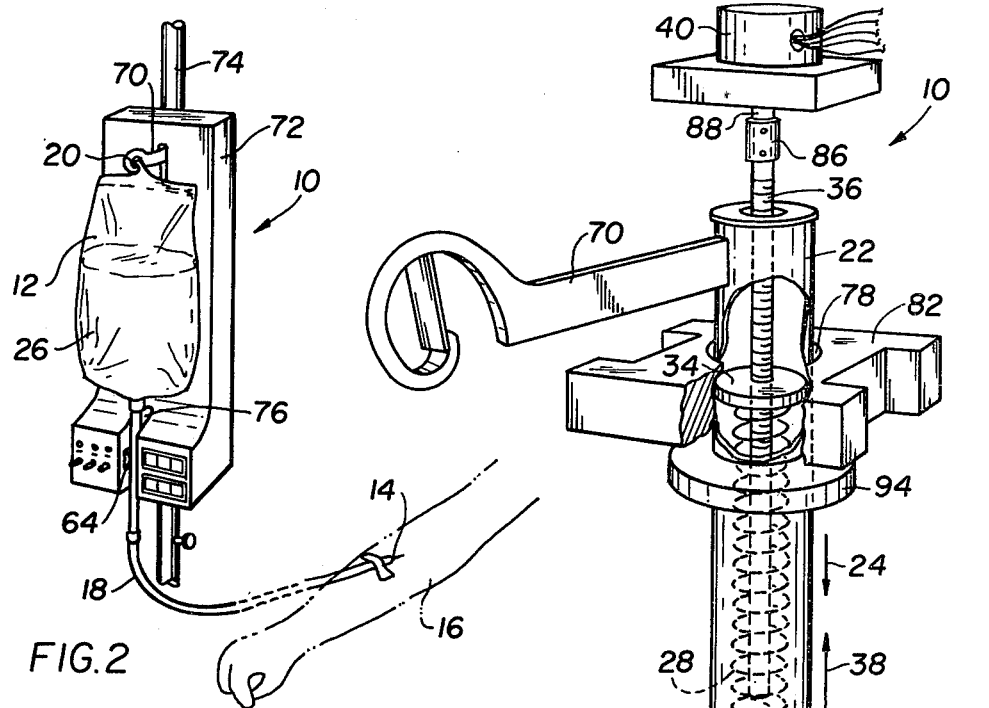
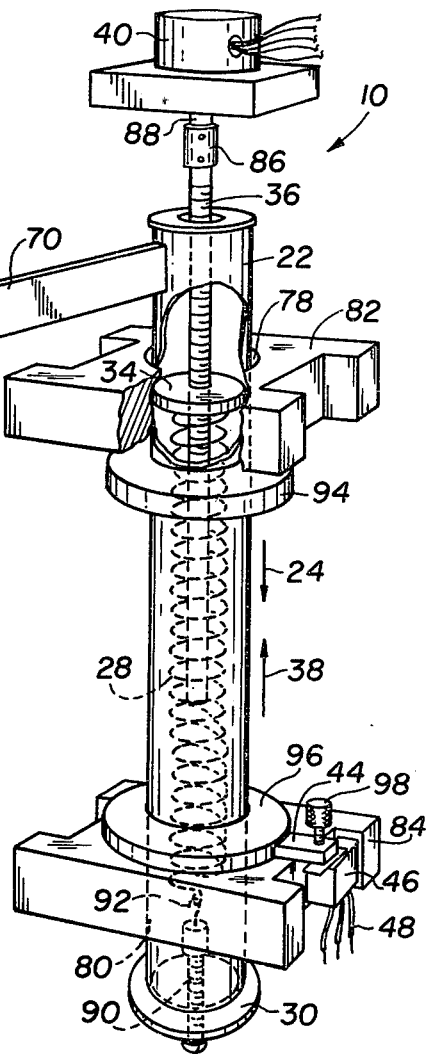
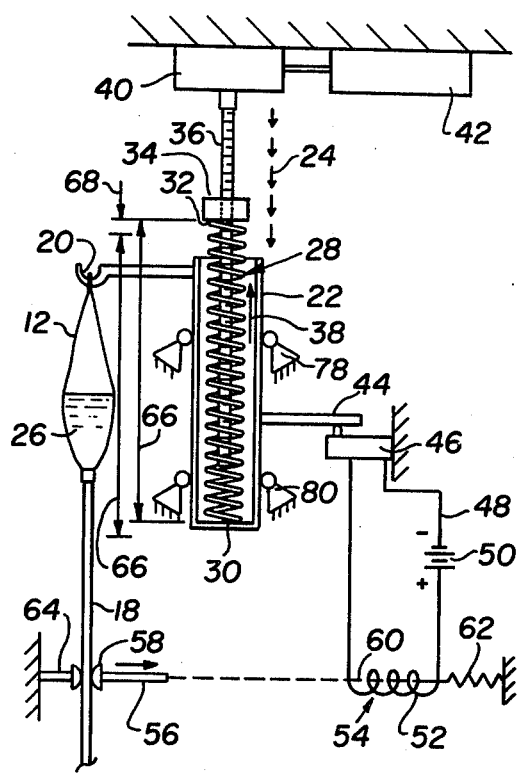
FIG. 2
FIG. 3

FLOW CONTROL FOR AN INTRAVENOUS FEEDING SYSTEM

The present invention relates generally to improvements for a system of intravenously feeding a patient, and more particularly, to flow control means for achieving the intravenous feeding, without imposing an additional burden of maintaining sterile conditions during such procedure, in a selected time interval.

For some medications and/or intravenous fluids, the dispensing thereof to the patient should be achieved in a specified time, an objective that is complicated by the particular arm position assumed by the patient, or similar circumstance, that may either promote or interfere with gravity feed of the intravenous fluid. Thus, an arm position that is unfavorable to gravity flow will prolong the feeding interval. While an apparent obvious solution is to deliver the intravenous fluid to a constant volume pump or the like for further delivery to the patient, this requires that the pump be sterile, as well as its conditions of operation, which may create more problems than are solved. Moreover, there are no known flow-controlling devices applicable to an intravenous feeding system for accomplishing the dispensing of the intravenous fluid in a selected time; although flow-control devices, as exemplified by the device of U.S. Pat. No. 3,390,238, which merely close the system when all the intravenous fluid has been dispensed is, of course, known. Such known devices, however, are limited in the manner noted in the results they can achieve.

A flow control for dispensing fluid intravenously to a patient demonstrating objects and advantages of the present invention is utilized in a known system including an elevated bottle or bag containing a supply volume of fluid and having a flexible hose connected from said bag to the patient. The flow control, per se, includes an electrically-operated clamp mounted in normally closed relation on the flexible hose so as to prevent flow therethrough. Dictating the open or closed condition of the clamp is a clamp-control circuit having a movable switch arm and a cooperating switch contact electrically connected to open said normally closed clamp whenever there is physical contact established between said movable switch arm and said switch contact. The aforesaid "physical contact," in turn, is determined by a cooperating pair of movement-urging means operatively connected to the switch arm in opposing relation to each other so as to position said switch arm in relation to the switch contact as a function of an overbalance in the urgency of one said means over the other. One said movement-urging means is a spring operatively connected to normally bias the switch arm in ascending movement into a clearance position above the switch contact; the other movement-urging means is the bag of the supply volume of fluid, said bag being operatively connected to normally bias the switch arm in descending movement into contact with the switch contact. A support means is provided for the spring which is effective to selectively cause ascending or descending movement in the spring while said spring is in a depending supported position therefrom. Completing the flow control is a timer operatively connected during the operation of the flow control to cause said support means to successively cause descending movement in the spring and thus also corresponding descending movement in the switch arm connected thereto. Constructed as just generally described, a cycle of operation of the flow control includes a first occurring descent in the switch arm as caused by the timer which opens the clamp and contributes to flow through the hose thereby emptying the bag of some fluid and causing corresponding diminishment in the force urgency thereof until there is an overbalance of spring urgency causing ascending movement in the switch arm. This "overbalance" thereupon again recloses the clamp until said timer thereafter causes a successive movement descent in the switch arm. The aforesaid "ascent" and "descent" provides an automatic cyclical operation to the flow control which controls flow on a "minute-by-minute" basis, or other timed basis, and thus enables the total dispensing of the intravenous fluid to be achieved within a selected period, or reasonably close to schedule.

The above brief description, as well as further objects, features and advantages of the present invention, will be more fully appreciated by reference to the following detailed description of a presently preferred, but nonetheless illustrative embodiment in accordance with the present invention, when taken in conjunction with the accompanying drawings, wherein:

FIG. 1 is a diagrammatic view of a flow control for an intravenous feeding system according to the present invention;

FIG. 2 is a perspective view illustrating structural features of a preferred embodiment thereof; and FIG. 3 is a perspective view, on an enlarged scale, of the major components of the within control illustrating further structural details thereof.

GENERAL DESCRIPTION OF MODE OF OPERATION

The within device is a flow control, generally designated 10, for fluid or other medication dispensed from an elevated bag 12 and fed or introduced intravenously, as at 14, into a patient 16 through a plastic tube 18. For any number of medical reasons it is desirable that the patient receive the fluid being dispensed within a specified time. For illustrative purposes, let it be assumed that bag 12 is filled with a volume of fluid that is required to be administered to the patient in 4 hours at a preferred flow rate of 1 cc per minute, which means that there is to be assumed to be approximately 240 ccs of fluid initially in the bag 12. The practicalities of the situation are such, however, that the patient during the 4 hours will move his arm 16 from position to position, some of which will promote, and some of which will inhibit, flow through the tube 18. It is primarily the function of the flow control 10 hereof to exercise supervising control over the flow rate through the tube 18 to provide the initially stated objective of causing the dispensing of all of the fluid in approximately 4 hours.

The above stated objective is, of course, obviously attainable using a pump or other flow metering device, rather than the flow control 10 hereof. The use of such pump or flow metering device is, however, not desirable because it introduces more serious problems than it solves. More particularly, when a flow controlling pump is used, this, of necessity, requires that the flow from the tube 18 be introduced into the pump, and delivered by the pump to the patient. To prevent infection or other serious physical harm to the patient, it is therefore necessary that the pump be scrupulously sterile and/or that the pump handle the intravenous fluid under, and in accordance with, strictly sterile conditions.

As will become more apparent as the description proceeds, the use of the flow control 10 hereof does not require any change in the usual manner in which intravenous feeding of the patient is accomplished with the usual source of supply or bag 12, hose 18 and intravenous needle 14. Stated another way, flow control 10 controls the volume of fluid dispensed through the tube 18 by selectively preventing or allowing flow therethrough, but this flow supervision is achieved entirely externally of the tube 18. In other words, a hose-pinching device at times minimizes or even completely blocks flow through the tube 18 or, when opened, allows unimpeded flow therethrough, and since this device is operated externally of the tube 18, the inherent sterile conditions of the intravenous feeding system 12, 18 and 14 are maintained intact.

Reference is now made to FIG. 1 illustrating diagrammatically the manner in which flow control 10 exercises supervising control over the flow of fluid feeding through the tube 18 from the intravenous bag 12. Being a diagrammatic illustration, FIG. 1 thus does not actually show flow control 10 as it actually exists in terms of its structural features, but it does show functionally how control 10 operates, and FIG. 1 to this extent is therefore useful in conveying an understanding of the invention. The actual structural features represented diagrammatically in FIG. 1 will be described subsequently in connection with FIGS. 2 and 3.

Referring to FIG. 1, flow control 10 includes an operative connection of bag 12, as at 20, to a vertically movable tube 22 and, as a result, tube 22 is continually being urged through descending movement 24 by the force or weight 26 of the intravenous fluid within the bag 12. Preventing the tube 22 from partaking of descending movement 24, however, is a helical spring 28 disposed internally of the tube 22 and connected at one end 30 to the bottom of the tube and, at its opposite end 32, to a nut 34 threadably engaged on a depending lead screw 36. In the specific condition of the components illustrated in FIG. 1, spring 28 attached to the elevated nut 34 is thus in a state of expansion which induces a force urgency in the direction 38 which is in opposition to the intravenous fluid weight 26 exerted in the direction 24. The urgency of spring 28 versus the fluid weight 26 can thus be thought of as being in equilibrium as depicted in FIG. 1.

To understand the mode of operation of flow control 10 which will soon be provided, it is necessary to appreciate that at its upper end the lead screw 36 is operatively connected to a stationarily mounted stepping switch motor 40 which, in turn, is electrically connected to a timer 42. The function of the timer 42 is to deliver an electrical pulse which is designed to cause a specific angular rotation of the motor. Thus, assuming a pulse is delivered every minute on the minute, said motor, when pulsed, is powered through a partial, full or other specific extent of rotation. The significance of the foregoing will soon be apparent.

Further structural features of the vertically slidable tube 22 include a switch arm 44 arranged to establish either a closed or opened electrical contact, in response to either descending or ascending movement of the tube 22, respectively, with a cooperating stationarily mounted switch contact 46. The two switch components 44, 46 are part of an electrical circuit 48 which includes its own battery or electrical source 50, and the field coil 52 of a solenoid valve 54. Valve 54 includes a plunger 56 which has a hose-pinching clamp 58 at one end and, at its opposite end, a piston 60 disposed within the field coil 52. Normally piston 60 is under the urgency of a spring 62 to close upon the intravenous feed tube 18 which occupies an interposed position between the clamp arm 58 and a cooperating opposing stationarily mounted clamp arm 64. Thus, as depicted and just described, circuit 48 operates as follows. Whenever the movable switch arm 44 is in a clearance position above and thus spaced from the switch contact 46, circuit 48 is broken and spring 62 is thus effective in urging the movable clamp 58 from right to left and thus in a direction in which this clamp closes upon the hose 18 and thereby terminates all flow through the hose. However, when switch arm 44 is allowed to descend into contact with contact 46, thus completing the circuit 48, electrical flow through this circuit and thus through the field coil 52 produces a magnetic field which urges the piston 60 from left to right. As a result, clamp arm 58 withdraws from its hose-pinching position into a clearance position, thereby allowing unimpeded flow through the intravenous hose 18.

Operation Of The Within Flow Control

Let it now be assumed that flow control 10 as diagrammatically depicted in FIG. 1 is to be used to supervise fluid flow through the intravenous hose 18 so that it generally proceeds at a rate of approximately 1 cc per minute. This, in turn, will allow the dispensing of the 240 ccs of intravenous fluid in approximately 4 hours, which is the general objective previously noted. There are three further start-up assumptions that will now also be noted. The first of these is that the elevation selected for the intravenous bag 12, and the diameter size of the intravenous hose 18 and intravenous needle 14 are selected so that they promote optimum conditions for gravity feed or flow by which it is readily possible to achieve movement of 1 cc of intravenous fluid through the system per minute. In fact, it is preferable that this volume of fluid be readily dispensed in slightly less than a minute.

The second start-up assumption has already been referred to. It is that motor 40 is intermittently operated by timer 42, this intermittent operation being one revolution per minute. This, in turn, means that there is corresponding operation of lead screw 36 at the rate of one revolution per minute.

The third assumption is that the pitch of the threads of the lead screw 36 is of a selected size so that it has a calibrated relation to the desired flow rate of 1 cc per minute. As will subsequently be explained, rotation of lead screw 36 is in that direction which results in descending movement of nut 34 threadably engaged thereon, the extent of this descending movement being related to one revolution of the lead screw 36 and thus being a distance that can be measured in terms of the pitch of the lead screw threads. Thus, as just noted, the pitch is selected to be of a size which results in that extent of descending movement in the nut 34 which in turn is calibrated to 1 cc of the intravenous fluid. The calibration in fact may be said to be related to 1 gram of the intravenous fluid, since the specific gravity of most medications is 1, and therefore 1 gram of the intravenous fluid is equivalent to 1 cc thereof.

At the start of the intravenous feeding of the patient it is contemplated that motor 40 will be operated to in turn power lead screw 36 in rotation in the direction which causes ascending movement in the nut 34. This is conducted until spring 28 is stretched so that the force urgency therein just equals or balances the weight 26 of the intravenous fluid in the bag 12. At this point of balance or equilibrium, it will be further understood that motor 40 is urged through one additional rotative turn that causes the lifting of the switch arm 40 from contact 46, thereby breaking the circuit 48 and causing spring 62 to, in turn, close clamp 58 upon the hose 18 shutting off any flow therethrough. Thus, in the starting condition of the intravenous system there is no feed communication to the patient, but the timer 42 commences its operation and soon changes this.

Specifically, after the first minute interval, timer 42 pulses motor 40 through one rotation and thus also the lead screw 36. As already noted, rotation of lead screw 36 is in that direction which causes nut 34 to descend the pitch distance of the threads of lead screw 36. Prior to this descent, however, it should be marked or noted that spring 28 is of an expanded length, designated 66, which produces a force urgency in the direction 38 which counterbalances the intravenous fluid weight 26 exerted in the opposite direction 24. After the single rotation of the lead screw 36, nut 34 descends the already noted pitch distance which, in FIG. 1 is designated 68. After this descent, the upper spring end 32 is of course lower than it was before, and so also is the spring lower end 30. Thus, the expanded length of spring 28 is still unchanged from the original length 66, but what has occurred is that it has been displaced downwardly the distance 68. Thus, the spring 28 is still in counterbalanced relation to the intravenous weight 26.

As a result of the downward displacement of spring 28, however, there necessarily also occurs displacement of the tube 22 the same corresponding distance 68. Displacement of tube 22 also results in descending movement in the switch arm 44 and this has the important result of establishing electrical contact between this arm and stationary contact 46 mounted in the path of descending movement thereof. Thus circuit 48 is completed resulting, as already noted, in the pulsing of the solenoid valve 54 into its open condition in which clamp 58 withdraws to a clearance position with respect to the hose 18. As a result, intravenous feeding is initiated through the hose 18. Assuming that the position of the patient and other ancillary conditions promote optimum flow, 1 cc of intravenous fluid will effectively be delivered through the hose 18 prior to the expiration of 1 minute. This, in turn, means that the intravenous fluid weight 26 is lessened by 1 gram and that the force urgency in spring 28 being exerted in the opposing direction 38 over-balances force 26, and thus causes ascending movement in the tube 22.

Ascending movement of tube 22 occurs until there is again a balance, or condition of equilibrium, established between the urgency of the spring 28 and the intravenous fluid weight 26. A significant consequence of the ascending movement is, of course, that switch arm 44 is lifted out of contact with switch contact 46, thus breaking the circuit 48. This, in turn, results in spring 62 closing the solenoid clamp 58 upon the hose 18, and thereby terminating intravenous feed through this conduit. Thus, under the assumed conditions of the patient maintaining a position promoting intravenous flow, the objective of 1 cc of intravenous fluid being delivered to the patient in 1 minute is readily achieved. At the expiration of the minute interval, timer 42 again pulses motor 40 and again results in descent of the tube 22 and in the closing of the circuit switch 44, 46 and the opening of the hose clamp 58, and thus in the resumption of intravenous feed movement through the hose 18. In this way, intravenous feeding is regulated on a minute by minute basis, and there is thus achieved the overall objective of dispensing of the total intravenous fluid in the total time duration allotted for this.

Before proceeding with a description of the actual structural features of flow control 10 that are depicted diagrammatically in FIG. 1, it is useful to consider the opposite alternative concerning the patient, namely that during a minute interval of operation that the patient's position and other conditions inhibit intravenous flow. Therefore, during a minute interval of operation, 1 cc of intravenous fluid may not exit from the intravenous bag 12. In this instance, therefore, weight 26 is heavier than it should be, and there is no ascending movement in the tube 22. Thus, the established electrical contact between switch arm 44 and contact 46 is maintained, thereby correspondingly maintaining the continuity of circuit 48. This, in turn, means that field coil 52 generates a magnetic field which holds piston 60 to the right, and that therefore clamp 58 remains withdrawn from the hose 18 and continues to allow intravenous feeding flow through this hose. This unimpeded flow is permitted for the entire minute interval. It may, in fact, be permitted for successive "minute" intervals since the various components of the control will assume operative positions that will allow intravenous feeding to automatically occur through the tube 18 for an extended period of time that ultimately will allow a cumulative volume of intravenous fluid to be dispensed to the patient so that actual feed can ultimately "catch up" to the desired feeding schedule. It is unlikely that during a four-hour period a patient will continuously maintain his hand in a position which minimizes gravity feed, such as a tiring position in which his hand is raised above his head, but that eventually another position will be assumed which will promote flow at 1 cc or more per minute. During any period of minimal flow, timer 42 nevertheless continues to cause intermittent operation of motor 40 and thus corresponding intermittent descending movement in discrete distances 68 in nut 34. While tube 22 cannot descend to the fullest extent theoretically possible, but only that distance at which switch arm 44 establishes contact with member 46, this does not interfere with spring 28 from being relaxed and, to this extent, there is thus a significant diminishment in the urgency that the spring is capable of exerting in the direction 38. The heavier than usual intravenous bag 12 will, therefore, over-balance the "relaxed" spring 28 and maintain switch arm 44 in electrical contact with member 46 and thus maintain conditions for unimpeded flow through the hose 18 throughout successive 1-minute intervals of operation as timed by the timer 42, and thus without the usual interruption of such flow which follows each descending movement of nut 34 as previously explained. The foregoing has the practical effect of giving the exiting gravity flow of intravenous fluid an opportunity to "catch up" with the desired optimum schedule for this exiting flow which was assumed to have been delayed by the poor hand position of the patient or such other cause. Ultimately, the continuous or uninterrupted exiting flow from the intravenous bag 12 will result in diminishment in the weight 26 to an extent which again counterbalances the urgency in the spring 28, thereby restoring supervising control over intravenous flow through the hose 18 to the control 10 on a minute by minute basis, as already described.

PREFERRED EMBODIMENT

The construction of a preferred embodiment of the within flow control 10 will now be described in connection with FIGS. 2 and 3. The intravenous bag 12 with its plastic tube 18 depending therefrom is suspended, as at 20, on a hook 70 which is operatively connected to the vertically slidable tube 22. As shown in FIG. 2, tube 22 and the other major components of the flow control 10 are preferably located within an external housing 72 which is mounted in an elevated position on a support rod 74. Thus, bag 12 is readily mounted at its upper end to the accessible hook 70 while its depending tube 18 extends through a slot 76 in the lower portion of the housing. Slot 76 is an advantageous location for the cooperating clamps 58, 64 which selectively open and close the flow passage of the tube 18 and thus control flow therethrough.

Although an appropriate construction for the flow control 10 hereof should be readily understood from the description thereof provided in connection with FIG. 1, for completeness sake reference should be made to FIG. 3 for an illustration of a preferred structural embodiment of the flow control 10. Specifically, in FIG. 3 it is illustrated how hook 70 extends laterally of tube 22 and how tube 22, in turn, is mounted both for ascending movement 38 and descending movement 24 by being disposed through upper and lower bearings 78 and 80, respectively, of stationary support brackets 82 and 84 which will be understood to be appropriately connected to the internal wall surfaces of the housing 72.

Also shown in FIG. 3 is the stepping switch motor 40 which will be understood to be stationarily mounted either to or adjacent the top of the housing 72. Appropriately connected, as at 86, to the rotor 88 of motor 40 is lead screw 36 which extends within the cylindrical tube 22. Nut 34 is illustrated as being threadably engaged to the lead screw 36 and is appropriately connected, as by soldering or the like, to the upper end of the helical spring 28 which, at its lower end, is connected to the bottom end 30 of tube 22. To allow adjustments in the tension of the spring 28, the connection at end 30 is advantageously made using a threaded member 90 threadably engaged to a spring-engaging hook 92.

Disposed as movement-limiting stops on the tube 22 are an upper disc 94 which limits ascending movement 38 in tube 22 to the point where it abuts against the bracket 82 and a lower disc 96 which limits descending movement 24 to the point where it abuts against the lower bracket 84. Advantageously mounted on the disc 96 is the switch arm 44. Appropriately stationarily mounted in the path of movement of arm 44 is the cooperating switch contact 46 of the solenoid circuit 48. To promote good electrical contact between the electrical components 44 and 46 switch arm 44 is provided with a threadably adjustable contact 98.

From the foregoing it should be readily appreciated that there has been described herein a system which allows supervising control to be exercised over the rate of flow of the intravenous fluid from source 12 to the patient 16. Even more important, the control is achieved by selectively opening and closing, and in this way monitoring and adjusting, a clamp 58, 64 which is externally applied to the delivery tube 18 and thus does not in any way detract from achieving under sterile conditions intravenous feeding using the intravenous equipment described herein. Although the flow control clamp 58, 64 is preferably electrically-operated, as described herein, it is contemplated that it can also be mechanically-operated. Similarly, when it was described that said clamp regulates the dispensing of intravenous fluid by terminating the flow thereof, it can also achieve the objective herein sought by minimizing the intravenous flow. In these and other respects, a latitude of modification, change and substitution is intended in the foregoing disclosure and in some instances some features of the invention will be employed without a corresponding use of other features. Accordingly, it is appropriate that the appended claims be construed broadly and in a manner consistent with the spirit and scope of the invention herein.

What is claimed is:

1. A flow control for dispensing fluid intravenously to a patient through a system including an elevated container of a supply volume of fluid and having a flexible hose connected from said container to said patient, said flow control comprising an electrically-operated clamp mounted in normally closed relation on said flexible hose so as to prevent flow therethrough, a clamp-control circuit having a movable switch arm and a cooperating switch contact electrically connected to open said normally closed clamp whenever there is physical contact established between said movable switch arm and said switch contact, a cooperating pair of movement-urging means operatively connected to said switch arm in opposing relation to each other so as to position said switch arm in relation to said switch contact as a function of an overbalance in the urgency of one said means over the other, one said movement-urging means being a spring operatively connected to normally bias said switch arm in ascending movement into a clearance position above said switch contact, the other said movement-urging means being said container of said supply volume of fluid operatively connected to normally bias said switch arm in descending movement into contact with said switch contact, a motor having a threaded rotor depending therefrom serving as a support means for said spring, said threaded rotor having a nut threadably disposed thereon and said spring being connected in a depending supported position from said nut such that in response to rotation of said threaded rotor said nut is either raised or lowered therealong to correspondingly either raise or lower said spring connected thereto, and a timer operatively connected to cause rotational operation of said motor so as to correspondingly cause rotation of said threaded rotor in relation to said nut to successively cause descending movement in said spring and thus also corresponding descending movement in said switch arm connected thereto, whereby a cycle of operation of said flow control includes a first occurring descent in said switch arm which opens said clamp and contributes to flow through said hose emptying said container of fluid and causing corresponding diminishment in the force urgency thereof until there is an overbalance of spring urgency causing ascending movement in said switch arm again re-closing said clamp.

2. An intravenous system flow control as claimed in claim 1 wherein the pitch of said threaded rotor is calibrated to the volume of said supply volume of fluid, whereby the extent of rotation of said rotor which occurs in response to the cyclical operation of said timer correspondingly determines the volume of fluid flow occurring during each cycle of operation.

* * * * *